(12) United States Patent
Lehmann et al.

(10) Patent No.: US 7,462,326 B2
(45) Date of Patent: Dec. 9, 2008

(54) DEVICE FOR THE DETECTION OF AT LEAST ONE LIGAND CONTAINED IN A SAMPLE THAT IS TO BE ANALYZED

(75) Inventors: Mirko Lehmann, Freiburg (DE); Claas Müller, Freiburg (DE); Holger Klapproth, Freiburg (DE); Ingo Freund, Vogtsburg-Oberrotweil (DE)

(73) Assignee: Micronas Holding GmbH, Freiburg (DE)

( * ) Notice: Subject to any disclaimer, the term of this patent is extended or adjusted under 35 U.S.C. 154(b) by 0 days.

(21) Appl. No.: 10/528,954

(22) PCT Filed: Sep. 26, 2003

(86) PCT No.: PCT/EP03/10736

§ 371 (c)(1),
(2), (4) Date: Mar. 22, 2005

(87) PCT Pub. No.: WO2004/031750

PCT Pub. Date: Apr. 15, 2004

(65) Prior Publication Data

US 2006/0051244 A1 Mar. 9, 2006

(30) Foreign Application Priority Data

Sep. 27, 2002 (DE) .................................. 102 45 435

(51) Int. Cl.
| | |
|---|---|
| *G01N 21/76* | (2006.01) |
| *G01N 21/00* | (2006.01) |
| *G01N 33/543* | (2006.01) |
| *G01N 21/41* | (2006.01) |
| *G02B 6/12* | (2006.01) |
| *G02B 6/00* | (2006.01) |
| *G02B 6/10* | (2006.01) |
| *G01B 9/02* | (2006.01) |
| *C12M 1/34* | (2006.01) |

(52) U.S. Cl. ....................... 422/82.11; 422/63; 436/172; 436/518; 435/287.2; 385/14; 385/12; 385/130; 356/128; 356/521

(58) Field of Classification Search .............. 422/82.11, 422/63; 204/403; 436/172, 518; 385/14, 385/12, 130; 356/128, 521; 435/287.2
See application file for complete search history.

(56) References Cited

U.S. PATENT DOCUMENTS 5,439,647 A * 8/1995 Saini ........................ 422/82.11

(Continued)

FOREIGN PATENT DOCUMENTS

DE 695 05 370 4/1999

(Continued)

OTHER PUBLICATIONS

Martin, Brett D. et al.; Direct Protein Microarray Fabrication Using a Hydrogel Stamper; Langmuir; Jul. 21, 1998; pp. 3971-3975; vol. 14, No. 15; American Chemical Society; United States.

*Primary Examiner*—Jill Warden
*Assistant Examiner*—Lore Ramillano
(74) *Attorney, Agent, or Firm*—The Webb Law Firm

(57) ABSTRACT

Disclosed is a device for detecting at least one ligand contained in a sample that is to be analyzed. Said device comprises an optical waveguide, on the surface of which at least one ligand-specific receptor is directly or indirectly immobilized. The ligand bonds to said receptor during contact therewith. The inventive device comprises at least one optical source of radiation for injecting excitation radiation into the waveguide, the radiation being used for exciting emission of luminescence radiation in accordance with the bonding of the ligand to the receptor. At least one radiation receiver is integrated into the semiconductor substrate of a semiconductor chip so as to detect the luminescence radiation. The waveguide is integrated in a monolithic manner into the semiconductor substrate or is applied thereupon as a wave-guiding layer.

20 Claims, 6 Drawing Sheets

U.S. PATENT DOCUMENTS

| | | | |
|---|---|---|---|
| 5,832,165 A | 11/1998 | Reichert et al. | |
| 5,936,730 A | 8/1999 | Huinan et al. | |
| 5,948,621 A | 9/1999 | Gaber et al. | |
| 5,959,292 A | 9/1999 | Duveneck et al. | |
| 6,126,899 A * | 10/2000 | Woudenberg et al. | 422/50 |
| 6,235,473 B1 | 5/2001 | Friedman et al. | |
| 6,287,874 B1 * | 9/2001 | Hefti | 436/501 |
| 6,312,961 B1 * | 11/2001 | Voirin et al. | 436/518 |
| 6,465,241 B2 * | 10/2002 | Haronian et al. | 435/287.2 |
| 2001/0000749 A1 | 5/2001 | Zinn et al. | |
| 2002/0135780 A1 * | 9/2002 | Budach et al. | 356/521 |

FOREIGN PATENT DOCUMENTS

| | | |
|---|---|---|
| DE | 19947616 | 5/2001 |
| DE | 10002566 | 8/2001 |
| DE | 695 26 438 | 10/2002 |
| EP | 0723146 | 7/1996 |
| WO | WO 9533197 | 12/1995 |
| WO | WO 9533198 | 12/1995 |
| WO | WO 9706422 | 2/1997 |
| WO | WO 9939829 | 8/1999 |
| WO | WO 00/43539 | 1/2000 |
| WO | WO 0184197 A | 11/2001 |
| WO | WO 02/89982 A2 | 5/2002 |

* cited by examiner

DEVICE FOR THE DETECTION OF AT LEAST ONE LIGAND CONTAINED IN A SAMPLE THAT IS TO BE ANALYZED

BACKGROUND OF THE INVENTION

1. Field of the Invention

This invention relates to a device for the detection of at least one ligand contained in a sample that is to be analyzed, with an optical waveguide, on the surface of which at least one receptor is directly or indirectly immobilized which, when it comes into contact with the ligand, forms a specific bond with the ligand, with at least one optical source of radiation for injecting excitation radiation into the waveguide, the radiation being used to excite the emission of luminescence radiation in accordance with the bonding of the ligand to the receptor, and with a semiconductor chip that has at least one radiation receiver on a semiconductor substrate to detect the luminescence radiation.

2. Description of the Prior Art

A similar device of the prior art is described in DE 100 02 566 A1. On the surface of a planar optical waveguide it has a plurality of measurement points at which specific nucleic acids are immobilized in the form of receptors. A liquid sample to be analyzed and that contains nucleic acids that are complementary to the receptors is placed in contact with the receptors. These nucleic acids bind to the specific receptors to which they are complementary. The receptor-ligand complexes that have nucleic acids that are complementary to each other are marked with a luminescent substance. By means of a laser diode, for example, an excitation radiation is generated and injected into the optical waveguide. An electromagnetic field, also called the evanescence field, is generated in a layer of the sample that is adjacent to the boundary surface by total reflection on the boundary surface of the waveguide. This field penetrates into the liquid sample to a depth of only a few hundred nanometers from the boundary surface. To emit luminescence radiation, the evanescence field excites almost exclusively the luminescent substance that is bonded to the surface of the waveguide. For the detection of the nucleic acids that are contained in the sample, the luminescence radiation is detected by means of a CCD camera with a high degree of local resolution. The CCD camera is located on the reverse side of the waveguide facing away from the receptors. It has an optical imaging system that images each of the individual measurement points located on the surface of the waveguide on the respective detector elements of a CCD sensor. The disadvantage of this device is that it still has a relatively large number of system components and is therefore correspondingly complex and expensive. An additional disadvantage is that the device is relatively large. Finally, the measurement sensitivity of the device leaves something to be desired.

The object of the invention is therefore to create a device of the type described above which makes it possible to have a compact size with a simple and economical construction.

SUMMARY OF THE INVENTION

The invention teaches that the waveguide is monolithically integrated with the semiconductor substrate or is located in the form of a waveguide layer on the semiconductor ship.

In that case, the at least one radiation receiver is located directly on the back side of the waveguide facing away from the receptor, and is thus at an appropriately short distance from the at least one receptor. The result is a very compact and flat device, which can have the shape of a wafer, for example. On account of the short distance between the receptor and the radiation receiver, there is no need for a complex and expensive optical imaging system between the receptor and the radiation receiver. The luminescence radiation emitted by a luminescent substance that has been deposited on the receptor can be detected over a large solid angle segment. The result is a device with a simple construction that can be manufactured economically and has high measurement sensitivity. The term "luminescence" as used here means all luminous phenomena such as fluorescence or phosphorescence that substances exhibit after quantum excitation.

In one preferred embodiment of the invention, the waveguide extends to over at least one radiation receiver, whereby the at least one receptor is preferably located on the surface of the waveguide directly opposite the radiation receiver. In that case, the luminescence radiation emitted by a ligand that is bonded to the receptor or by a luminescent substance located on the receptor runs approximately orthogonally to the direction of extension of the waveguide, which achieves an effective transmission of the luminescence radiation through the waveguide into the radiation receiver. The luminescence radiation is therefore conducted directly to the radiation receiver without detours or bypasses, as a result of which a high detection sensitivity of the device is made possible.

It is advantageous if the waveguide layer is directly adjacent to the semiconductor chip, and if the topography of the semiconductor chip in the area of the semiconductor chip directly adjacent to the waveguide is realized so that the boundary surface opposite the at least one receptor between the semiconductor chip and the waveguide runs between two planes that are oriented parallel to the plane of extension of the semiconductor chip and the distance between said two planes is less than the wavelength of the excitation radiation, and in particular less than one-half, preferably one-quarter and optionally one-eighth of the wavelength of the excitation radiation. In the vicinity of the waveguide, therefore, the topography of the semiconductor chip is essentially plane, which makes possible a low-loss guidance of the excitation radiation in the waveguide. In a corresponding manner, the boundary surface of the waveguide that faces the receptors can also run between two planes that are oriented parallel to the plane of extension of the semiconductor chip, whereby the distance between said planes is less than the wavelength of the excitation radiation, and in particular less than one-half, preferably one-quarter and optionally one-eighth of the wavelength of the excitation radiation. The semiconductor chip can have an oxide layer at the boundary surface to the waveguide.

In one advantageous embodiment of the invention, located between the semiconductor chip and the waveguide is an intermediate layer, the optical index of refraction of which is less than that of the waveguide, whereby the intermediate layer has the negative shape of the surface structure of the semiconductor chip on its back side facing the semiconductor chip and on its back side which is in contact with the semiconductor chip, and whereby the front side of the intermediate layer that forms the boundary surface with the waveguide is plane. It is thereby even possible for the waveguide to extend continuously or without interruption over the at least one radiation receiver and/or the structures for the electronic circuit. During the manufacture of the device, the intermediate layer is preferably produced by first fabricating the semiconductor chip with the at least one radiation receiver and then optionally the structures for the electronic circuit on a wafer, and then depositing on the wafer a liquid medium containing the material for the intermediate layer using a centrifuge process. After the medium has been uniformly distributed on the wafer by the centrifugal force, it solidifies to form the intermediate layer. The waveguide is then deposited on top of it. The medium can contain a volatile solvent such as toluene, for example, and a polymer such as PMMA, for example. Spin-on glass can also be used as the liquid medium, however.

In one advantageous embodiment of the invention, the intermediate layer is realized in the form of an adhesive layer, preferably in the form of a polymer layer. In that case, the waveguide can then be manufactured economically and in large quantities in the form of an injection-molded plastic part. The waveguide can be a thin plastic or glass wafer which is adhesively attached to the semiconductor substrate during the manufacture of the device. The waveguide can also serve as a protective cover for the semiconductor chip. The waveguide can optionally extend over the entire semiconductor chip.

In an additional realization of the invention, the waveguide is connected with the semiconductor chip by means of at least one bonding point. In this embodiment, too, the waveguide can be a thin plastic wafer that is preferably less than one millimeter thick.

In one advantageous realization of the invention, the waveguide is realized in the form of a thin-film coating which is preferably made of a transparent polymer, and in particular polystyrene. The at least one receptor is thereby preferably located directly on the thin-film layer. However, the waveguide can also be made of another material, for example spin-on glass. Using thin-film technology, the waveguide can be manufactured so that it is less than 100 micrometers thick. Therefore, a correspondingly large percentage of the luminescence radiation emitted by the luminescent substance bonded to the receptor will then strike the radiation receiver. For the detection of the ligands in the sample, only a small amount of the sample is therefore required. For the manufacture of the device, the waveguide can be deposited in a simple manner on the waveguide by immersion-coating or using the centrifuge method.

In one particularly advantageous embodiment of the invention, the waveguide is also formed by a metal oxide layer, in particular a silicon dioxide ($SiO_2$) layer or a tantalum pentoxide ($Ta_2O_5$) layer. In that case, the waveguide can be manufactured economically using standard processes for semiconductor manufacturing, such as plasma oxidation or chemical vapor deposition (CVD), for example. The thickness of the waveguide can thereby be less than 10 micrometers, so that almost half of the luminescence radiation emitted by a luminescent substance bonded to the surface of the waveguide strikes the radiation receiver. The result is a correspondingly high measurement sensitivity, which means that only extremely small quantities of sample material are required for an analysis of the sample. The oxide layer can have a surface structure to which at least one receptor adheres directly. Consequently there is no longer any need for a layer of adhesion promoter between the waveguide and the at least one receptor. It is also possible, however, for the waveguide to be realized in the form of a silicon nitride ($Si_3N_4$) layer.

It is particularly advantageous if the optical radiation source is realized in the form of a semiconductor radiation source and is integrated into the semiconductor chip. In that case, the device makes possible an even more compact and economical construction. The semiconductor radiation source can be a laser diode or an LED that emits the excitation radiation preferably in a narrow-band wavelength range in which the at least one radiation receiver is insensitive.

In one preferred embodiment of the invention, for the injection of the excitation radiation into the waveguide, an optical injection system is provided in the emission area of the optical radiation source, and is preferably realized in one piece with the waveguide and has, among other things, at least one prism, one optical lattice and/or a deflecting mirror. The radiation source can be located on the back side of the wave guide facing away from the receptors, with its emission side facing the optical injection system of the waveguide. The excitation radiation emitted by the radiation source is thereby deflected by the optical injection system so that it enters into the waveguide at an angle which is selected so that the radiation is guided by taking advantage of the total reflection in the waveguide. The result is a low-loss guidance of the excitation radiation from the radiation source to the at least one receptor.

It is advantageous if a plurality of radiation receivers integrated into the semiconductor substrate next to each other, preferably in the form of rows or a matrix, if at least one detection field that has at least one receptor is located in the detection range of the individual radiation receivers. In that case, the device makes possible a detection of the receptor-ligand complexes on the surface of the waveguide as well as a resolution of their individual locations. The individual detection fields can have different receptors, so that the sample can be tested simultaneously for the presence of a plurality of different ligands. It is also conceivable, however, that at least one group of detection fields can have the same receptors. The measurements from the individual radiation receivers of the group can then be averaged, filtered and/or compared to one another for control purposes. If the concentration of the ligand in the sample is to be determined by means of the device, it is advantageous if the receptors of at least two detection fields have a different affinity for the ligands. The concentration of the ligand can then be measured in a broad concentration range, without having to dilute or concentrate the sample to perform the measurement. The waveguide can extend over the radiation receiver without interruptions or discontinuities, which means that a masking step can be eliminated during the manufacture of the waveguide.

The detection fields are thereby at some distance from one another and are positioned relative to the radiation receivers so that the individual radiation receivers receive essentially no luminescence radiation from a detection field of another radiation receiver. Thus a high crosstalk attenuation is achieved between the measurement systems consisting of the individual detection fields and the individual radiation receivers associated with each of them.

In one advantageous realization of the invention, the at least one receptor is located in the interior cavity of a flow-through chamber that has at least one inlet opening and one outlet opening, whereby the semiconductor substrate preferably forms a wall area of the flow-through measurement chamber. In the flow-through measurement chamber, biomolecules or biocomponents can then be tested and can be supplied with a nutrient fluid by means of the inlet and outlet openings. The biomolecules can be nucleic acids or derivatives thereof (DNA, RNA, PNA, LNA, oligonucleotides, plasmids, chromosomes), peptides, proteins (enzyme, protein, oligopeptiide, cellular receptor proteins and complexes thereof, peptide hormones, antibodies and fragments thereof), carbohydrates and derivatives thereof, in particular glycolized proteins and glycosides, fats, fatty acids and/or lipids.

To control the temperature of the flow-through measurement chamber, a heating and/or cooling device can be provided which preferably has a Peltier element. The heating device is preferably realized in the form of a thin-film heater. The device can thereby be used for multiple purposes by raising the temperature in the flow-through measurement chamber after a measurement to a point where all of the ligands bonded to the receptors are released from the receptors. In that case, the ligands can also be flushed out of the flow-through measurement chamber by feeding in a flushing medium via the outlet opening. The flushing process is thereby continued until the radiation receivers no longer detect any luminescence radiation. Then a new sample can be introduced into the flow-through measurement chamber via the inlet opening and tested. However, the device can also be used for the determination of the melting point and/or the bonding constants of a ligand such as a DNA sequence, for example. The bonding of the ligand to the receptors is thereby measured as a function of temperature and/or time. The melting point of the DNA sequence can also be determined from the melting curve measured as indicated above, i.e. the temperature at which one-half of an originally double-stranded DNA sequence is present in the form of a single strand. By means of the melting point it is possible to recognize mutations in DNA sequences which can occur in genetically transmitted illnesses, for example.

In one appropriate realization of the invention, at least one reagent and/or reaction partner is stored in the flow-through measurement chamber to detect the bonding of the at least one ligand to the at least one receptor. The flow-through measurement chamber is then ready for use, i.e. to perform the measurement, the only further action that is necessary is to feed the sample to be tested into the measurement chamber via the inlet opening. The reagent and/or the reaction partner is preferably lyophilized and can be impressed on the inside wall of the measurement chamber, for example. Preferably there is also a stabilizing agent such as trehalose, poly (2-hydroxyethyl) methacrylate (pHEMA) or bovine serum albumin (BSA).

Several exemplary embodiments of the invention are explained in greater detail with reference to the accompanying drawings, some of which are highly schematic:

DETAILED DESCRIPTION OF THE PREFERRED EMBODIMENTS

Figure 1:
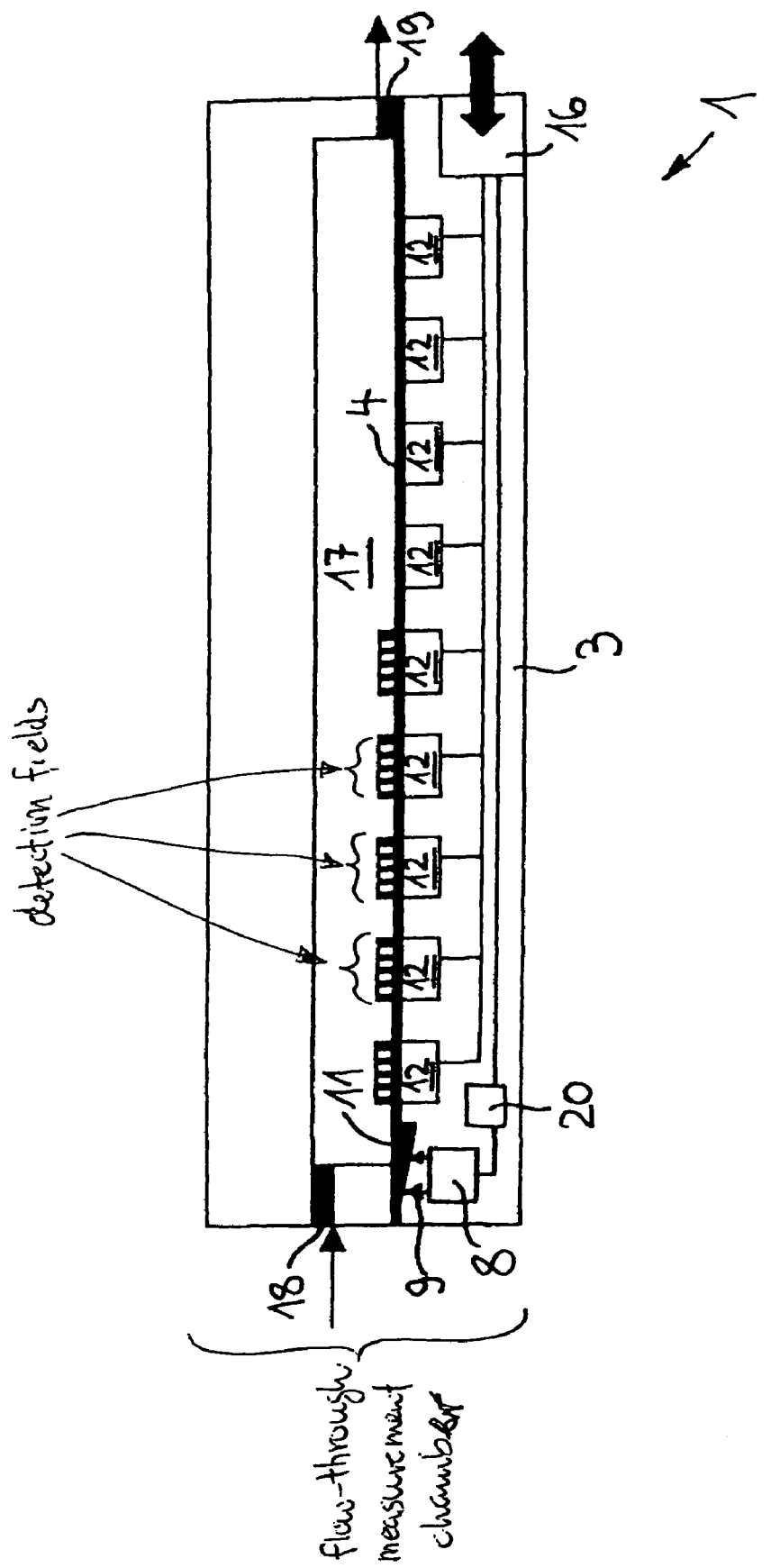
FIG. 1 is a cross section through a device for the detection of ligands contained in a sample to be tested, with a flow-through measurement chamber.

A device designated 1 overall for the detection of at least one ligand 2 contained in an essentially liquid sample to be tested has a semiconductor chip 3 which is integrated using methods from the semiconductor engineering industry with an optical waveguide 4 (FIG. 1). The waveguide can be made of a polymer material, for example.

Figure 2:
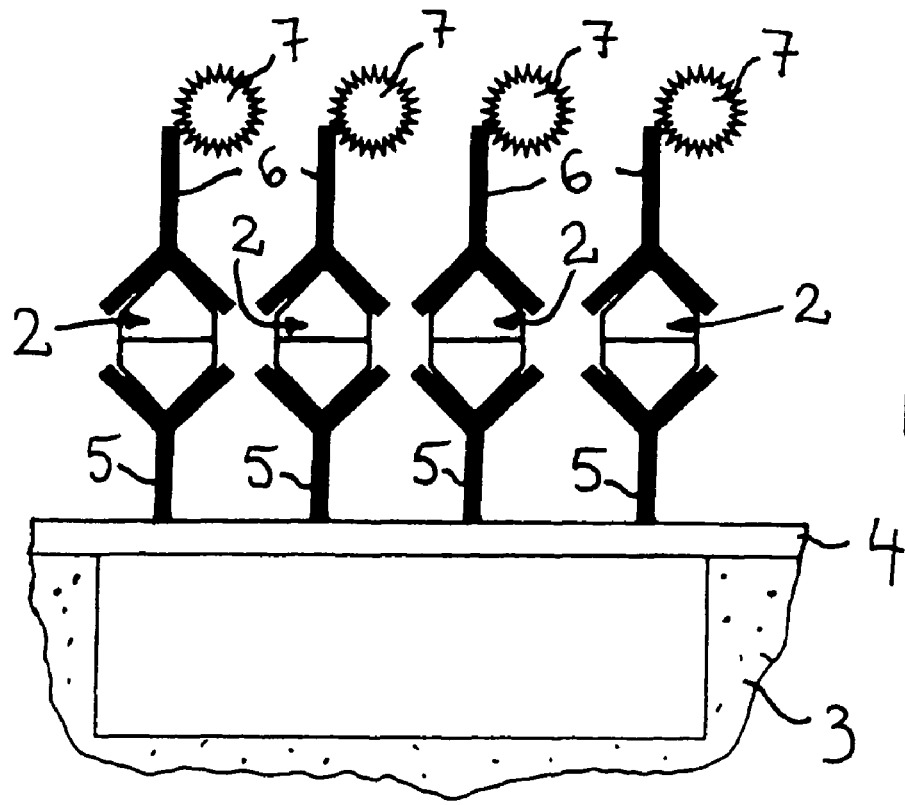
FIG. 2 and FIG. 7 show a cross section through a wall area of the flow-through measurement chamber that has an optical waveguide, whereby immobilized on the waveguide are receptors to which ligands are bonded which are indirectly marked with a luminescent substance.

FIG. 2 shows that on the surface of the waveguide 4, receptors 5 are immobilized that, when they come into contact with the ligand 2, bind to it. The receptors can be immobilized by silanization, for example, or by a polyimide layer located on the waveguide 4, to which the receptors adhere. The receptors 5 can be imprinted on the waveguide 4 on the polyimide layer or on the polyimide layer located on the waveguide 4. In the exemplary embodiment illustrated in FIG. 2, the receptors 5 are antibodies to a specified epitope of the ligand 2. After the bonding of the epitope to the receptor 5, the antibody complex thus formed, consisting of the epitope and the receptor 5, is marked by means of a second antibody 6 that bonds to the first epitope. This antibody 6 is directly or indirectly marked with a luminescent substance 7.

FIG. 1 shows that an optical semiconductor radiation source 8, such as a laser diode or LED, for example, is integrated into the semiconductor chip 3. The spectrum of the radiation 9 emitted by the radiation source 8 has at least one excitation wavelength at which the luminescent substance 7 is excited to the emission of luminescence radiation 10. For the injection of the excitation radiation 9 into the waveguide 4, in the emission range of the radiation source 8 there is an optical injection system 11, which has microprisms (not illustrated in any further detail in the drawing), which deflect the excitation radiation emitted by the radiation source 8 so that it is guided utilizing the total reflection in the waveguide 4. As a result of the total reflection at the boundary surface of the waveguide 4, an electromagnetic field is produced in the optically thinner medium, namely the sample, as a result of which the luminescent substances 7 bonded to the surface of the waveguide 4 are excited to emit luminescence radiation 10. Because the evanescence field penetrates into the sample by a depth of only a few hundred nanometers, the luminescent substances 7 that are excited to emit the luminescence radiation 10 are almost exclusively those on the surface of the waveguide, while the unbonded luminescent substances 7 in the sample contribute practically nothing to the luminescence radiation.

For the detection of the luminescence radiation there are a plurality of optical radiation receivers 12 integrated into the semiconductor ship 3, whereby all of the radiation receivers 12 are realized in the form of semiconductor components. The radiation receivers 12 are located on the back side of the waveguide 4, which is permeable to the luminescence radiation 10 and faces away from the receptors 5. The luminescence radiation 10 therefore strikes an optical imaging system on the radiation receivers 12 directly, i.e. without the interposition of an optical imaging system. The device thereby has a compact and economical construction.

The luminescent substance 7 is an upward-converting luminescent substance. Luminescent substances of this type are described in EP 0 723 146 A1. Examples of upward-converting luminescent substances include the BND pigment by Dyomics GmbH, Jena, and IR-140. In contrast to downward-converting luminescent substances, upward-converting luminescent substances do not acquire the energy needed for the quantum emission from a single quantum effect, but from multiple quantum effects. Downward-converting luminescent substances, in comparison to downward [sic] converting luminescent substances therefore have a significantly greater Stokes shift, at which the wavelength of the exciting radiation can be approximately twice as great, for example, as the wavelength of the luminescence radiation. It is thereby possible to provide, as the radiation source, an infrared semiconductor radiation source 8 which makes possible a high level of radiation intensity with compact dimensions. The infrared light from such semiconductor radiation sources 8 also has the advantage that fewer scatter effects occur than with short-wave optical radiation. By means of the upward-converting luminescent substance 7, the optical radiation emitted by the radiation source 8 can be converted into visible light or near-infrared light, to which the radiation receivers 12 have a high detection sensitivity. The radiation receivers 12 are insensitive to the excitation radiation 9.

Figure 3:
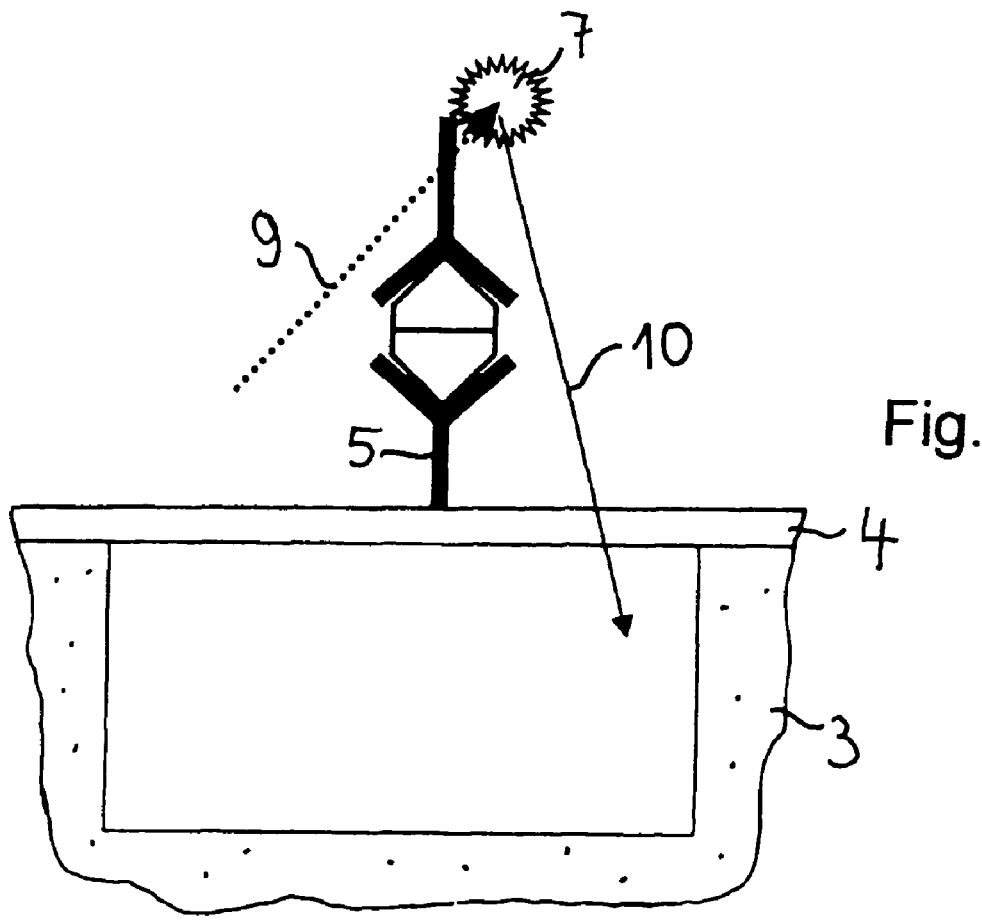
FIG. 3 is an illustration like the one presented in FIG. 2, whereby the luminescent substance is excited by means of excitation radiation to emit luminescence radiation, and whereby the excitation and the luminescence radiation are illustrated schematically in the form of beams.

FIGS. 2 and 3 show that the waveguide 4 extends to over the radiation receiver 12 and that the receptors 5 are located on the surface of the waveguide 4 directly opposite the radiation receiver 12. Thus the luminscence radiation 10 can travel directly from the luminescent substance 7 to the radiation receivers 12.

Figure 4:
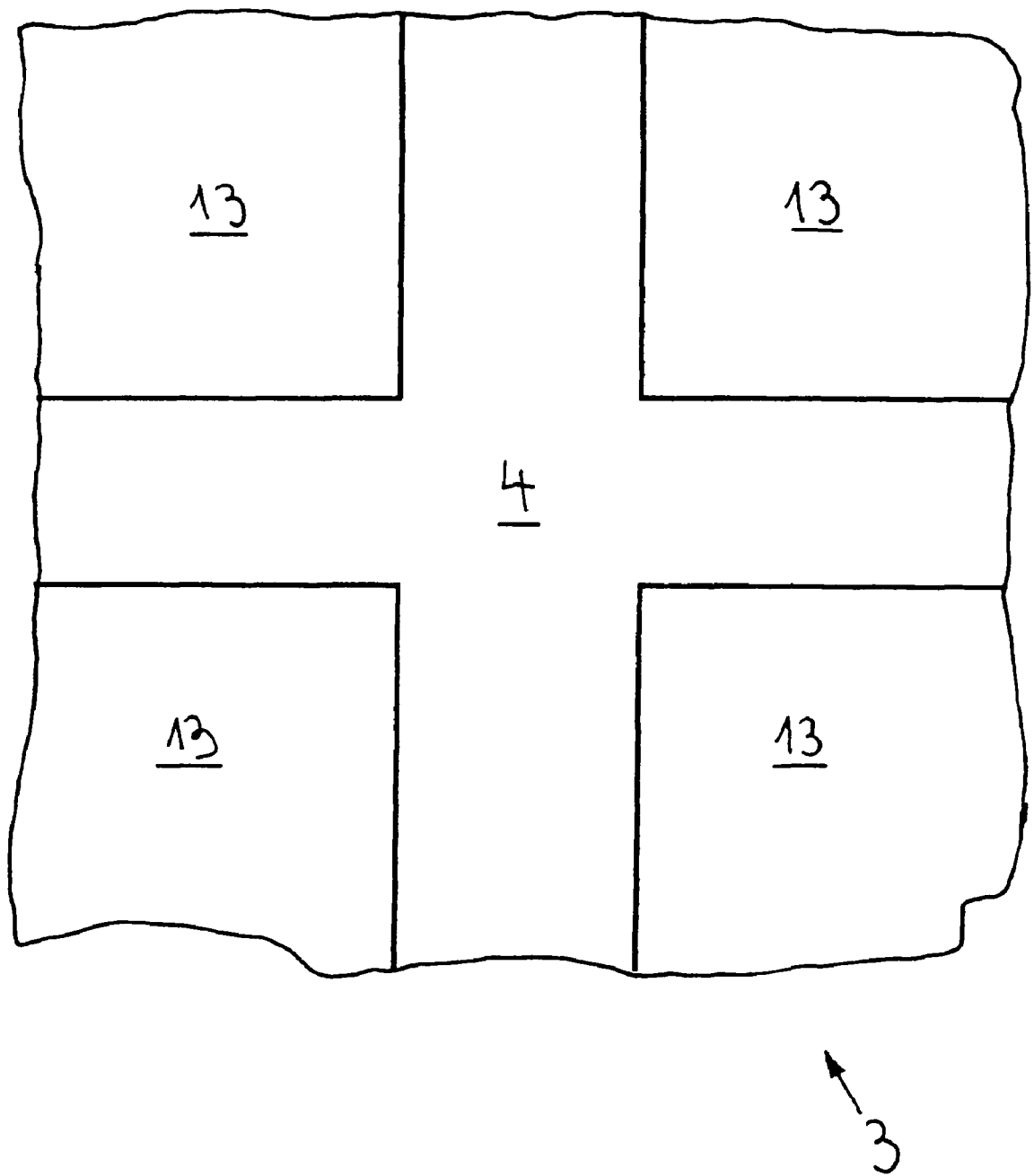
FIG. 4 is an overhead view of a portion of a semiconductor chip.
Figure 5:
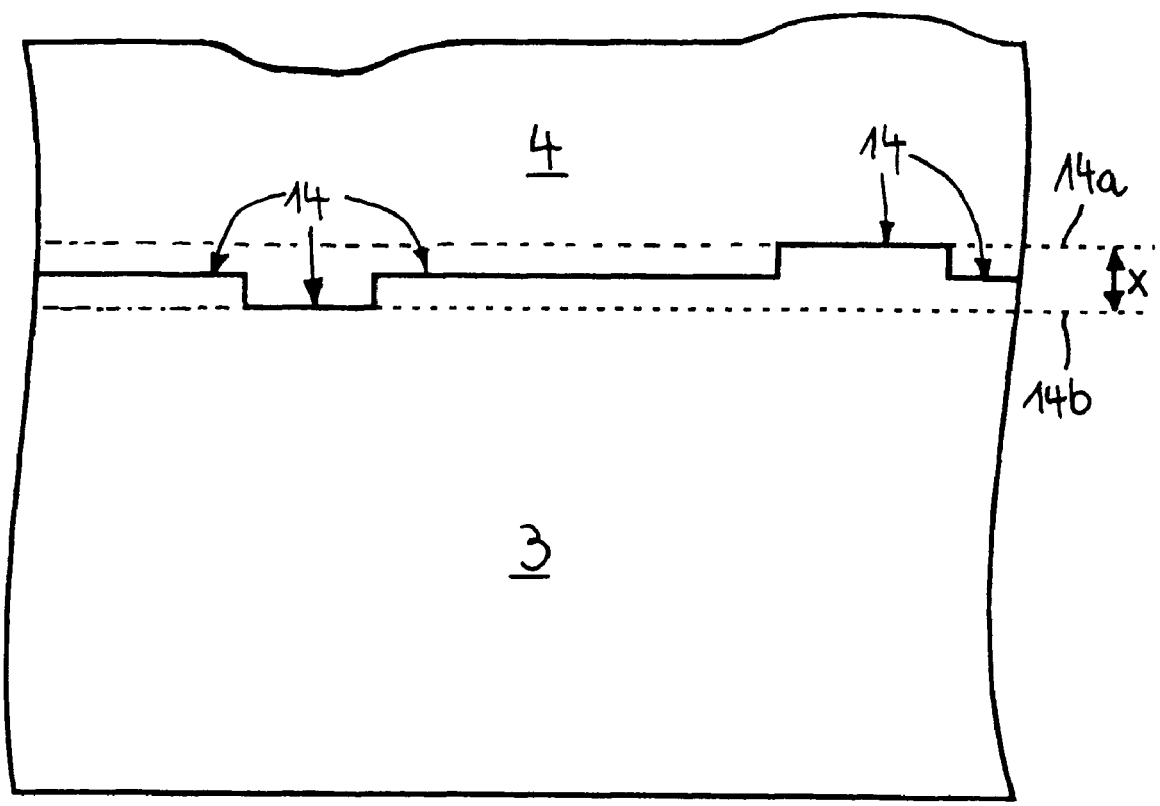
FIG. 5 is a cross section through a portion of the semiconductor chip and the waveguide located on it.

In the exemplary embodiment illustrated in FIGS. 4 and 5, the waveguide 4 is directly adjacent to the semiconductor chip 3. The waveguide 4 has interruptions in which structures 13 for an electronic circuit are located. This circuit has printed conductors that are connected with the radiation receivers 12. The topography of the semiconductor chip in the area of the semiconductor chip adjacent to the waveguide 4 is realized so that the boundary surface 14 opposite the receptors 5 between the semiconductor chip 3 and the waveguide 4 runs between two imaginary planes 14a, 14b that are each oriented parallel to the plane of extension of the semiconductor chip 3, whereby the distance x between said planes is less than one-eighth of the wavelength of the excitation radiation 9. This arrangement almost completely prevents an undesirable light extraction out of the waveguide 4 at the boundary surface 14. Structures that require a surface topography of the semiconductor chip 3 that is different from a plane, such as printed conductors made of aluminum, for example, are essentially located laterally next to the waveguide 4. In the exemplary embodiment illustrated in FIG. 5, the waveguide 4 is formed by a semi-metal oxide layer, which extends over an area near the surface on a semiconductor substrate 3 of the semiconductor chip 3 and runs approximately parallel to the plane of extension of the semiconductor substrate. The semiconductor substrate can be made of silicon, for example.

Figure 6:
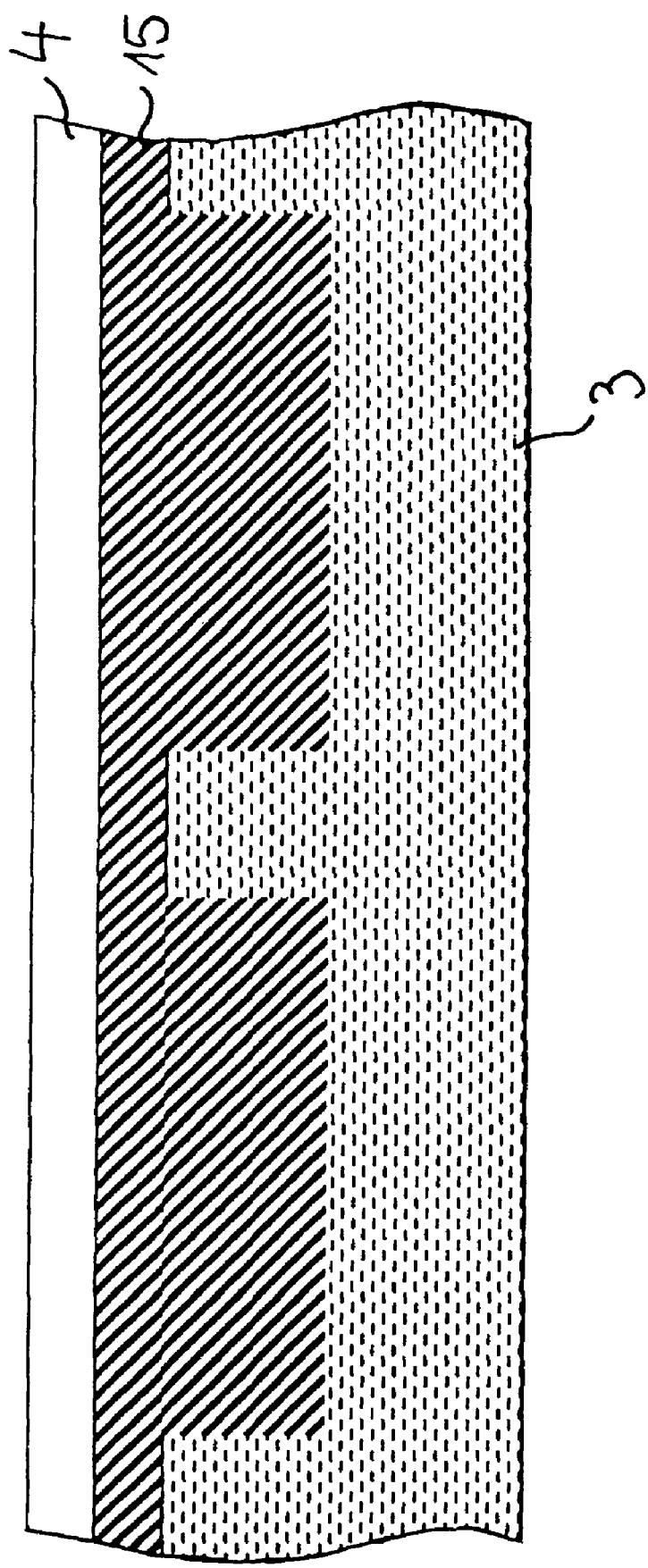
FIG. 6 is an illustration similar to the one in FIG. 5 although an intermediate layer is located between the waveguide and the semiconductor chip.

In the exemplary embodiment illustrated in FIG. 6, between the semiconductor chip 3 and the waveguide 4, there is an intermediate layer 15 that runs approximately parallel to the plane of extension of the semiconductor chip 3 and the optical index of refraction of which is less than that of the waveguide 4. The intermediate layer 15 is directly adjacent to the semiconductor chip 3 and has the negative shape of the semiconductor chip 3. This shape can be achieved, for example, if the material for the intermediate layer 15 is deposited during the manufacture of the device 1 in liquefied form on the semiconductor chip 3 using the centrifuge process and—after it has been distributed uniformly over the surface of the semiconductor chip 3—has solidified. On its side facing away from the semiconductor chip 3, the intermediate layer 15 is flat. The waveguide 4 is deposited on the intermediate layer 15 in the form of an additional layer. The result is a flat boundary surface between the intermediate surface 15 and the waveguide 4, which makes possible a largely loss-free guidance of the excitation radiation 9 in the waveguide 4. The waveguide 4 can thereby extend continuously over the semiconductor chip 3.

FIG. 1 shows that the radiation receivers 12 are connected by means of printed conductors with an actuator and analysis device 16 that is integrated into the semiconductor chip. The analysis device 16 has an interface device that is schematically indicated in the drawing for connection with a higher-level display and/or analysis unit, such as a microcomputer, for example.

Figure 7:
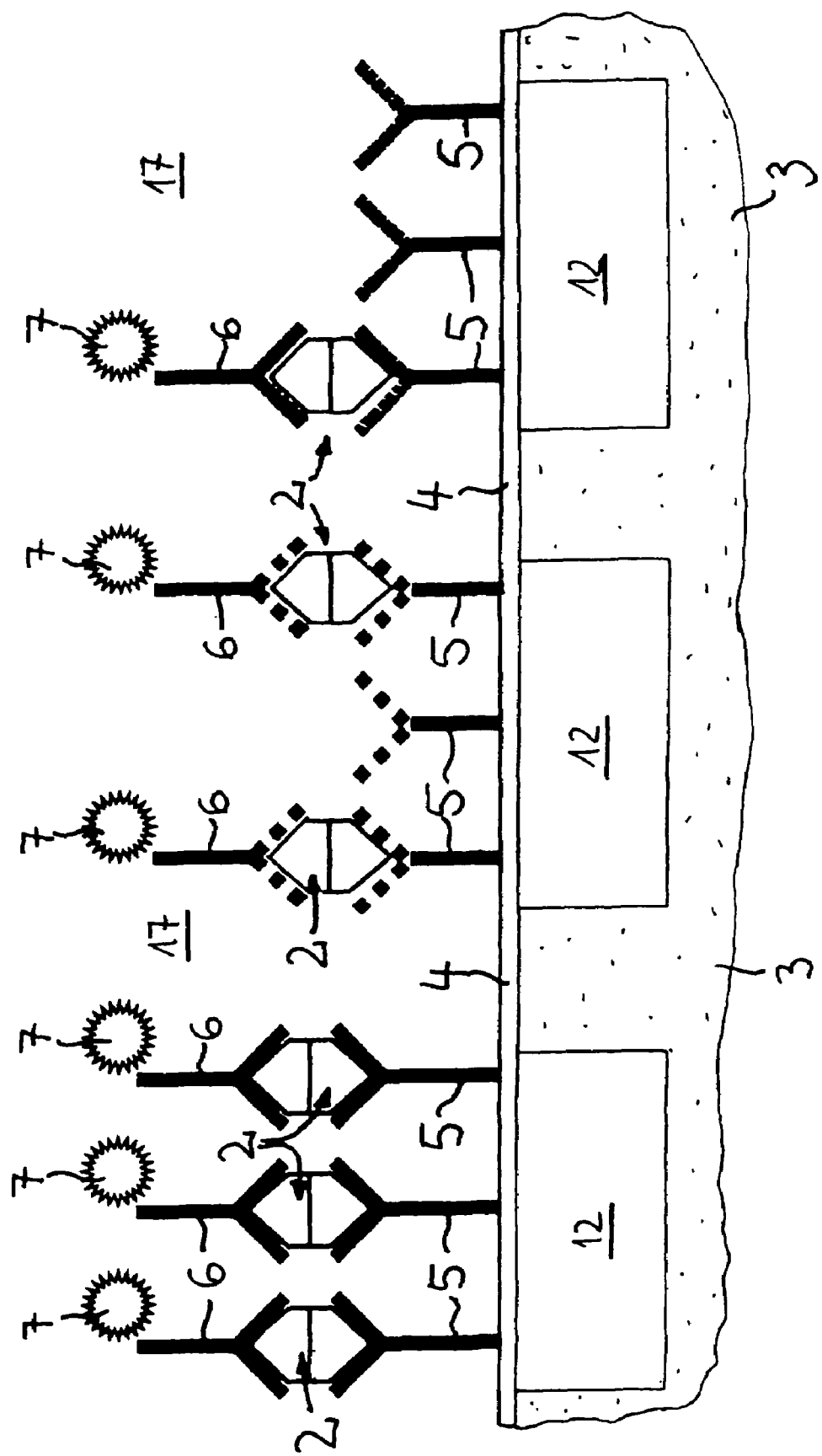

FIG. 7 shows that a plurality of radiation receivers 12 are integrated next to one another in the form of a matrix in the semiconductor substrate. In the detection range of the individual radiation receivers 12, each detection field is located with a plurality of receivers 5. The individual detection fields have different receivers 5, each of which can enter into a bond with a specified ligand 2.

In FIGS. 2 to 4, the receptors are shown on a larger scale than the radiation receivers 12. The distances between detection fields that are next to one another on one hand and the distances between the luminescent substances 7 bonded to the receptors 5 and the radiation receivers 12 associated with them are selected so that the individual radiation receivers 12 can receive essentially no luminescence radiation from a detection field of a neighboring radiation receiver.

FIG. 1 shows that the semiconductor chip 3 forms a wall area of a flow-through measurement chamber, in the interior cavity 17 of which the receptors 5 are located. The flow-through measurement chamber has an inlet opening 19 and an outlet opening 18. The inlet opening 19 is connected with a feed line for the sample, which is not shown in any detail in the drawing, and the outlet opening 18 is connected with a discharge line.

It should also be mentioned that the radiation source 8 is connected, for the modulation of the excitation radiation 9, with a modulation device 20, which is integrated into the semiconductor chip 3. By means of the modulation device 20, the excitation radiation 9 can be turned on and off in cycles, for example, to take into consideration in the analysis any signal components that may be caused by spurious light or non-specific optical excitation. For this purpose, the modulation device 20 must be connected with the analysis device 16 by means of a connecting line.

The device 1 for the detection of at least one ligand 2 contained in a sample to be analyzed therefore has an optical waveguide 4, on the surface of which at least one receptor 5 that is specific for the ligand 2 is directly or indirectly immobilized. When the ligand 2 comes into contact with the receptor 5, it bonds to the receptor. The device 1 has at least one optical radiation source 8 for the injection of excitation radiation 9 into the waveguide 4. The radiation 9 is used to excite the emission of luminescence radiation 10 as a function of the bonding of the ligand 2 to the receptor 5. For the detection of the luminescence radiation 10, at least one radiation receiver 12 is integrated into the semiconductor substrate of a semiconductor chip 3. The waveguide 4 is monolithically integrated with the semiconductor substrate or is applied to the semiconductor substrate in the form of a waveguide layer.

The invention claimed is:

1. A device for the detection of at least one ligand contained in a sample that is to be analyzed, said device comprising:
    an optical waveguide defining a single light path along which multiple detection fields and multiple radiation receivers are disposed, each detection field including at least one receptor for contacting a ligand to form a specific bond with the ligand;
    at least one optical source of radiation for injecting excitation radiation into the waveguide, the radiation being used for exciting the emission of luminescence radiation as a function of the bonding of ligands to receptors; and a semiconductor chip having said radiation receivers on a semiconductor substrate, each detection field having one radiation receiver associated therewith, each radiation receiver operative for detecting only the luminescence radiation sent out by the detection field associated therewith, wherein:

the waveguide is monolithically integrated with the semiconductor substrate or is in the form of a waveguide layer located on the semiconductor chip; and the radiation receiver associated with each detection field is integrated into the semiconductor substrate facing the detection field directly on the back side of the waveguide facing away from the detection field.

2. The device of claim 1, wherein the semiconductor chip includes a boundary surface opposite the receptors between the semiconductor chip and the waveguide, the boundary surface running between two planes that are oriented parallel to the plane of extension of the semiconductor chip, wherein the distance between the two planes is less than the wavelength of the excitation radiation.

3. The device of claim 2, wherein the distance between the two planes is less than either one-half, one-fourth or one-eighth of the wavelength of the excitation radiation.

4. The device of claim 1, wherein the semiconductor chip, laterally next to the waveguide, has an electronic circuit.

5. The device of claim 1, wherein:

between the semiconductor chip and the waveguide there is an intermediate layer, the optical index of refraction of which is less than that of the waveguide;

a side of the intermediate layer adjacent the semiconductor chip conforms to a surface of the semiconductor chip; and a side of the intermediate layer adjacent the waveguide is essentially plane.

6. The device of claim 5, wherein the intermediate layer is an adhesive coating.

7. The device of claim 6, wherein the adhesive coating is a polymer coating.

8. The device of claim 1, wherein the waveguide is connected with the semiconductor chip at least at one bonding point.

9. The device of claim 1, wherein the waveguide is a thin-film layer of a transparent polymer material.

10. The device of claim 9, wherein the polymer material is polystyrene.

11. The device of claim 1, wherein the waveguide is a metal oxide layer.

12. The device of claim 11, wherein the metal oxide layer is either a silicon dioxide layer or a tantalum pentoxide layer.

13. The device of claim 1, wherein the optical radiation source is a semiconductor radiation source that is integrated into the semiconductor chip.

14. The device of claim 1, further including an optical injection system provided in the emission area of the optical radiation source for deflecting optical radiation emitted by the optical radiation source to the waveguide.

15. The device of claim 14, wherein:

the optical injection system is part of the waveguide; and the optical injection system includes at least one of the following: a prism, an optical lattice and/or a deflecting mirror.

16. The device of claim 1, wherein the detection fields are spaced from one another and are positioned relative to the radiation receivers so each radiation receiver receives essentially no luminescence radiation from a detection field of an other radiation receiver.

17. The device of claim 1, wherein:

the receptors are located in an interior cavity of a flow-through measurement chamber that has at least one inlet opening and one outlet opening; and the semiconductor chip defines a wall area of the flow-through measurement chamber.

18. The device of claim 17, further including a heating and/or cooling device for controlling a temperature of the flow-through measurement chamber.

19. The device of claim 18, wherein the heating and/or cooling device is a Peltier element.

20. The device of claim 17, wherein the flow-through measurement chamber includes at least one reagent and/or reaction partner for the detection of the bonding of at least one ligand to at least one receptor.

* * * * *